US010420512B2

(12) United States Patent
Greiser et al.

(10) Patent No.: US 10,420,512 B2
(45) Date of Patent: Sep. 24, 2019

(54) DYNAMIC MAGNETIC RESONANCE IMAGING WITH VARIABLE CONTRAST

(71) Applicant: Siemens Aktiengesellschaft, Munich (DE)

(72) Inventors: Andreas Greiser, Erlangen (DE); Michaela Schmidt, Uttenreuth (DE); Peter Speier, Erlangen (DE); Aurelien Stalder, Erlangen (DE); Michael Zenge, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 1075 days.

(21) Appl. No.: 14/681,454

(22) Filed: Apr. 8, 2015

(65) Prior Publication Data
US 2015/0282764 A1   Oct. 8, 2015

(30) Foreign Application Priority Data
Apr. 8, 2014  (DE) .................. 10 2014 206 724

(51) Int. Cl.
*A61B 5/055* (2006.01)
*A61B 5/00* (2006.01)
(Continued)

(52) U.S. Cl.
CPC .......... *A61B 5/7214* (2013.01); *A61B 5/0044* (2013.01); *A61B 5/055* (2013.01);
(Continued)

(58) Field of Classification Search
CPC ..... A61B 5/7214; A61B 5/0044; A61B 5/742; A61B 5/055; A61B 2576/00; G01R 33/56509; G01R 33/56325; G01R 33/50
See application file for complete search history.

(56) References Cited

U.S. PATENT DOCUMENTS

2003/0225328 A1   12/2003   DeMeester et al.
2005/0189942 A1    9/2005   Tsao et al.
(Continued)

FOREIGN PATENT DOCUMENTS

CN   101238979 A    8/2008
JP   2005278919 A   10/2005
(Continued)

OTHER PUBLICATIONS

Kellman et al.: "Extracellular volume fraction mapping in the myocardium, part 1: evaluation of an automated method", in Journal of Cardiovascular Magnetic Resonance, BioMed Central, vol. 14; No. 1 (2012).
(Continued)

*Primary Examiner* — Ruth S Smith
(74) *Attorney, Agent, or Firm* — Schiff Hardin LLP

(57) ABSTRACT

In a method for computing MR images of an examination object that performs a cyclic movement, MR signals are detected over at least two cycles of the cyclic movement. In each of these cycles, data for multiple MR images are recorded. Over these cycles, a magnetization of the examination object that influences the MR images approaches a state of equilibrium in a second of these cycles is closer to the state of equilibrium than in a first of these cycles. Movement information for various movement phases of the cyclic movement of the examination object is determined using the MR images from the second cycle, with movement information of the examination object determined for each of the various movement phases. Movement correction of the examination object is carried out in the MR images of the first cycle using the movement information determined in the second cycle.

14 Claims, 4 Drawing Sheets

(51) Int. Cl.
  *G01R 33/50* (2006.01)
  *G01R 33/563* (2006.01)
  *G01R 33/565* (2006.01)

(52) U.S. Cl.
  CPC .............. *A61B 5/742* (2013.01); *G01R 33/50* (2013.01); *G01R 33/56325* (2013.01); *G01R 33/56509* (2013.01); *A61B 2576/00* (2013.01)

(56) References Cited

U.S. PATENT DOCUMENTS

| | | |
|---|---|---|
| 2005/0245812 A1 | 11/2005 | Kim et al. |
| 2006/0241379 A1 | 10/2006 | Greiser et al. |
| 2007/0088212 A1 | 4/2007 | Takei et al. |
| 2008/0150532 A1 | 6/2008 | Slavin et al. |
| 2008/0187180 A1 | 8/2008 | Yui |
| 2008/0242973 A1 | 10/2008 | Warmuth |
| 2011/0251477 A1 | 10/2011 | Schmitt |
| 2012/0133747 A1 | 5/2012 | Takahashi et al. |
| 2012/0189183 A1 | 7/2012 | Xue et al. |
| 2013/0134976 A1 | 5/2013 | Sugiura |
| 2013/0272591 A1* | 10/2013 | Xue .................... G06T 11/003 382/131 |
| 2013/0278259 A1* | 10/2013 | Greiser ................ G01R 33/50 324/309 |
| 2015/0099964 A1 | 4/2015 | Voigt et al. |

FOREIGN PATENT DOCUMENTS

| | | |
|---|---|---|
| JP | 2012115319 A | 6/2012 |
| WO | 2011058047 A1 | 5/2011 |

OTHER PUBLICATIONS

Tsai et al; "Free-breathing MOLLI: Application to myocardial $T_i$ mapping"; Medical Physics, AIP,; No. 12; pp. 7291-7302 (2012).

Santini et al; "Fast simultaneous T1 and T2 mapping of the heart"; Proceedings of the International Society for Magnetic Resonance in Medicine, ISMRM, 21st Annual Meeting and Exhibition, Salt Lake City, Utah, p. 4561; (2013).

Kellman et al., "Motion-Corrected Free-Breathing Delayed Enhancement Imaging of Myocardial Infarction," Magnetic Resonance in Medicine, vol. 53 (2005), pp. 194-200.

Setser et al., "Cine Delayed-Enhancement MR Imaging of the Heart Initial Experience," Radiology, vol. 239 (2006), pp. 856-862.

Schmitt et al., "Inversion Recovery TrueFISP: Quantification of T1, T2, and Spin Density," Magnetic Resonance in Medicine, vol. 51 (2004), pp. 661-667.

Guetter et al., "Efficient Symmetric and Inverse-Consistent Deformable Registration Through Interleaved Optimization," Siemens Corporate Research, Princeton, NJ (2011) pp. 590-593.

Stalder et al., "Cardiac Multi-Contrast CINE: Real-Time Inversion-Recovery Balanced Steady-State Free Precession Imaging with Compressed-Sensing and Motion-Propagation," ISMRM, vol. 5667 (2014), p. 1.

Greiser et al., "Cardiac Motion-Corrected Inversion Prepared Real-Time ("TIRT") Cine TrueFISP Imaging for Rapid Myocardial T1 Estimation," ISMRM, vol. 5473 (2012), p. 1.

* cited by examiner

DYNAMIC MAGNETIC RESONANCE IMAGING WITH VARIABLE CONTRAST

BACKGROUND OF THE INVENTION

Field of the Invention

The present invention relates to a method for computing MR images of an examination object which executes a cyclic movement and to an MR apparatus for this purpose.

Description of the Prior Art

In the acquisition of MR images of moving organs, the inherent movement of the organ, of the heart for example, must be taken into account and possibly the movement of the organ overall as a result of the movement of the surroundings. This is the case for movement of the heart or of the liver during breathing, wherein this second movement is expectedly a repetitive and almost periodic movement. A first option for the imaging of moving objects is a technique known as the single-shot technique, in which the raw data space (k-space) is read out (filled) completely after the application of an RF pulse and in which the recording of the data is fast enough to freeze the movement. The further recording option is the segmented recording technique, in which the data recording for an image is divided into a number of movement cycles and MR data are recorded only in comparable movement phases. During heart imaging, the breathing and the heart movement must be taken into account. The movement caused by breathing can be minimized by breath-holding techniques or frozen by navigator gating. The first option limits the measurement duration and the second option limits efficiency and increases complexity.

One option for data recording is the so-called CINE data recording for the measurement of the heart muscle movement, in which many MR images for each heart cycle are recorded, and wherein a good constant contrast between heart muscle and blood is needed. This means using a sequence with a good T2/T1 contrast. Another option of image recording is a static tissue characterization, in which the tissue characteristics are determined by measurement of one image per heartbeat. This process usually involves a preparation block in the overall operating sequence, such as a saturation pulse or inversion pulse or a T2 preparation, followed by an optional wait time and the subsequent image data acquisition. The contrast needed for the characterization is created by the preparation block.

Furthermore, the use of contrast media is known, and the tissue characterization can be carried out with or without the use of contrast media. T1 contrasts before and after application of contrast media are of especial significance. An important tissue characterization at the heart is the presentation of scar tissue by a technique known as delayed-enhancement, in which, five to ten minutes after administration of contrast medium, data for a T1-weighted image are recorded such that the healthy myocardium no longer emits any signal, but the scar delivers a bright signal.

SUMMARY OF THE INVENTION

It is desirable to develop a recording technique in which a representation of the movement of an organ that is moving, and a tissue characterization with the necessary contrast, can be combined.

In accordance with the invention, a method for computing MR images of an examination object that performs a cyclic movement is provided, wherein MR signals for recording of MR images of the examination object over at least two cycles of the cyclic movement are detected and wherein, in each of the at least two cycles, data for multiple MR images are recorded. In this method, the magnetization of the examination object influencing the MR images approaches a state of equilibrium over the at least two cycles and, in a second cycle of the at least two cycles, the magnetization is closer to the state of equilibrium than it is in the first cycle of the at least two cycles. Furthermore, movement information for various movement phases of the cyclic movement of the examination object is determined using the multiple MR images from the second cycle such that movement information of the examination object is determined for each of the various movement phases. Subsequently, a movement correction of the examination object in the MR images of the first cycle for the various movement phases of cyclic movement is carried out using the movement information determined in the second cycle and this is done such that, for the various MR images of the first cycle a movement-corrected MR image for the various movement phases of the cyclic movement is computed.

Through the use of the MR images in the second cycle, in which the magnetization is close to the state of equilibrium, the movement information can be reliably determined, since the contrast change in this series of MR images of the second cycle is now small. It is thus possible to compute the movement information, which can be deformation information for example, reliably with the MR images in the second cycle. This movement information is then transferred to the MR images in the first cycle in which the magnetization is further away from the state of equilibrium. This means that the individual MR images in the first cycle differ more strongly in contrast. Since now, with the aid of the movement information, movement-corrected MR images for the various movement phases of the cyclic movement are computed, MR images are obtained for the various movement phases of the cyclic movement and for various contrasts. Furthermore, it is no longer necessary to define before image recording which contrast or which phase of the cyclic movement is of interest, since this choice can be determined retrospectively after the recording of the MR images since MR image series have been computed for various contrasts.

The use of the movement information from the second cycle is not restricted to a single first earlier cycle. The movement information from the second cycle can also be applied to MR images from a number of cycles lying before this second cycle. Expressed in a different way, the movement information of the second cycle can be applied to the MR images of at least one cycle lying before said cycle in time. Furthermore incomplete cycles can be included, meaning that not all MR images of a cycle have to be used. Furthermore the start point of the cycles or the start point within the cycles can be freely selectable for determining movement.

For the computation, it is possible that for each of the various movement phases of the examination object in the second cycle a movement change relative to each of the other movement phases in the second cycle is determined. A movement correction can then be carried out in the MR images of the first cycle such that, for each movement phase of the cyclic movement, a movement-corrected MR image is determined in the first cycle and this is done for each MR image of the first cycle. Through this movement information of each movement phase to all other movement phases, MR images for the various movement phases in the first cycle can then be computed from the movement information and the MR images recorded in the first cycle, which then also have different contrasts.

A contrast value is preferably assigned to each MR image here, with which the examination object is presented in the associated MR image. Here a contrast change between temporally adjacent MR images of the first cycle is greater than for temporally-adjacent MR images of the second cycle. Since the magnetization in the recording of the MR images in the second cycle is closer to the state of equilibrium than in the first cycle, the contrast differences between the individual MR images in the first cycle are greater than in the second cycle. If it is now assumed that each MR image recorded in the first cycle has a different contrast value and each recorded MR image of the first cycle can be assigned to a movement phase, then at least one MR initial image is produced for the various contrast values of the first cycle in each case that was recorded for an associated contrast value as an MR image. Now, using the MR image recorded at the associated contrast value which was recorded for one of the movement phases and using the movement information for the various movement phases for the various contrast values of the first cycle, movement-corrected MR images for the various movement phases are calculated from the other missing movement phases. These then have the same contrast value as the associated initial image.

The MR images recorded in the first cycle each have a different contrast value. For an existing contrast value, with the aid of the movement information obtained in the second and the recorded MR image in the first cycle, the initial image, the movement-corrected MR images for the respective other movement phases can be computed. Thus, for this one contrast value, a series of MR images is available which show the movement of the examination object for the same contrast. When this is repeated for the other contrast values of the images of the first cycle, then an image sequence for the various contrast values is obtained, so that for different contrast values from the image sequence so-called moving or CINE recordings can be created in any given way.

After the computation of the movement-corrected MR images, MR images for all contrast values of the first cycle and for all movement phases of the cyclic movement which have either been recorded or computed are present. Thus MR images of the cyclic movement can be considered for any given contrast values after the recording.

In a form of embodiment the magnetization of the examination object is prepared before the detection of the MR signals by applying a preparation pulse, wherein the magnetization then approaches the state of equilibrium over the at least two cycles. Before the start of the actual imaging with the switching of the gradient and RF pulses, there can be a preparation, by an inversion pulse for example, in that the magnetization is inverted by 180°. If the image recording then takes place with fast gradient echo sequences, for example a bSSFP sequence (balanced steady-state free precession), then the contrast differs in the individual MR images at the start, strongly in the first cycle directly after application, whereas it then only changes slightly from MR image to MR image in the second cycle.

Instead of preparation with an inversion pulse a saturation pulse can also be applied, in that the magnetization is saturated before the recording of the MR signals and finally then moves again into the state of equilibrium. However the application of an inversion or saturation pulse is not necessary. In another form of embodiment such a course of magnetization is able to be achieved, if for example a gradient echo sequence is used over and over again with a repetition time TR which is smaller than the T1 time. Here as well, the magnetization reaches a state of equilibrium after a while.

Preferably, the first cycle is the temporally first cycle in the cyclic movement, in which the MR signals of the examination object are recorded, wherein the second cycle is preferably the last cycle in which the MR signals of the examination object are recorded. In the last cycle the magnetization is very close to the state of equilibrium, while the magnetization in the first temporal cycle still changes most strongly.

If the examination object is the heart for example, the MR signals can be recorded over a number of heart cycles, for example a number between 3 and 6, preferably 4 or 5. Since a heart cycle lasts for around one second, the recording of the MR images is possible within three to around six seconds. Even persons in ill health being examined can hold their breath for this period of time. Depending on the area of application, more than six cycles can also be used. Only a number of cycles ≥2 is necessary.

For a recording of many MR images within one heart cycle it is possible to record the MR images with the aid of acceleration methods, for example compressed-sensing technology. As is known, this technique continues to reduce the echo time, in that certain conditions of the recorded MR data are exploited in order to reduce the number of raw data points actually recorded.

It is further possible to create locally-resolved T1 and T2 relaxation maps of the examination object from the computed and recorded MR images for the various contrast values. If for example an inversion pulse was used, then the T1 or T2 time can be deduced with the intensity curve in the individual MR images. These can then be computed pixel-by-pixel and displayed for the various movement phases.

The invention likewise relates to an MR apparatus for computing the MR images with a recording unit for recording the MR signals and creating the MR images over the at least two cycles of the cyclic movement, as explained above, and with a processing unit, which, as explained in detail above, computes the movement information for the various phases of the cyclic movement with the use of the MR images from the second cycle and applies this to the MR images in the first cycle, in order to compute MR images for the various movement phases of the movement for the MR images in the first cycle which have various contrast values.

DESCRIPTION OF THE PREFERRED EMBODIMENTS

Figure 1:
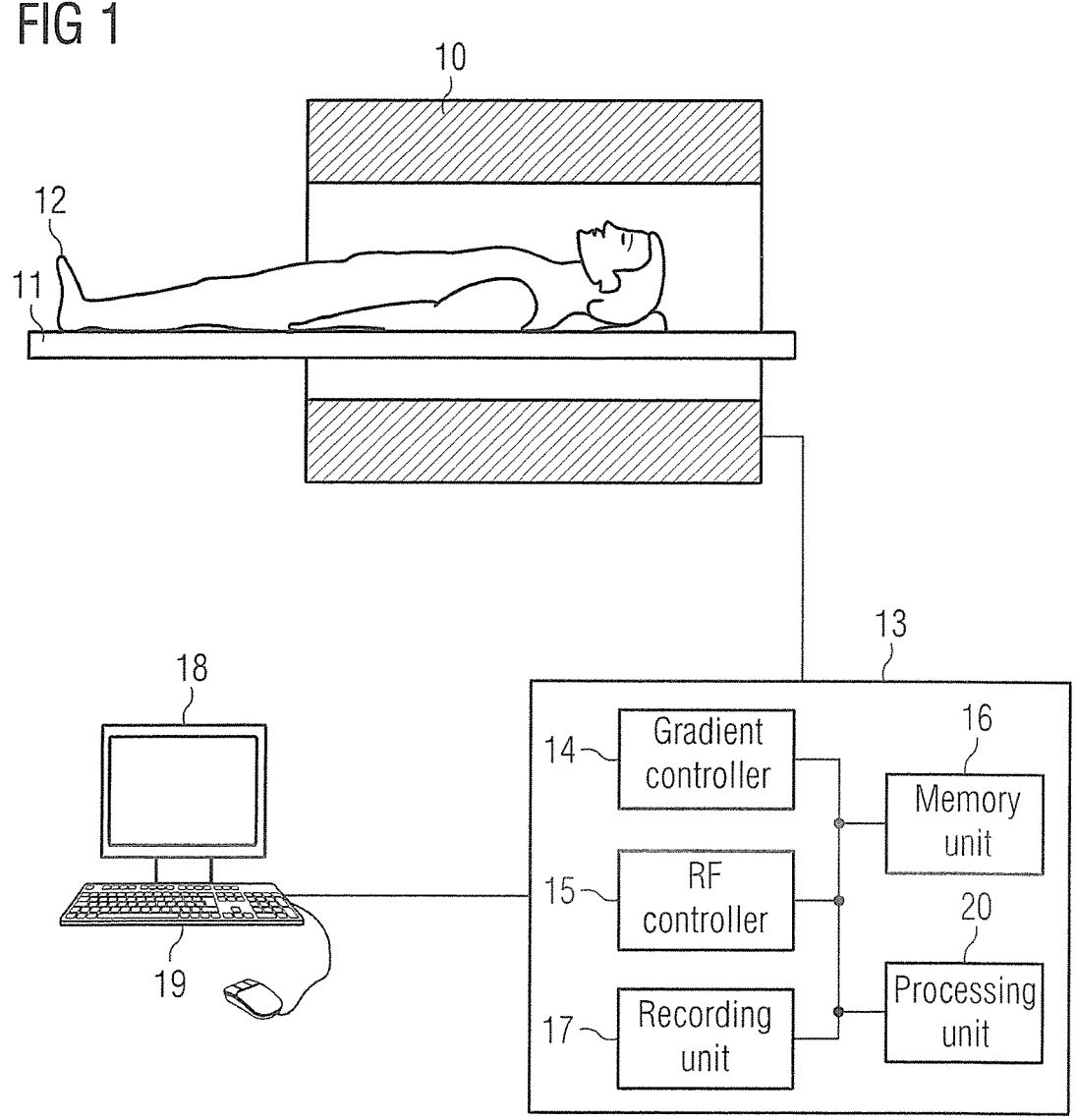
FIG. 1 shows an MR apparatus that is operable in accordance with the invention for the recording and computation of MR images with variable contrast in short periods of time.

FIG. 1 shows a schematic of a magnetic resonance apparatus, with which, in accordance with the invention, MR images of an examination object, such as an organ which executes a cyclic movement, can be created with different contrasts. The magnetic resonance apparatus has a magnet 10 for creating a polarization field $B_O$, wherein a person being examined 12, located on a bed 11, is moved into the center of the magnet, in order for locally-encoded magnetic resonance signals from an examination object to be recorded there. By applying radio-frequency pulses and switching of magnetic field gradients, the magnetization created by the polarization field $B_0$ can be deflected from the state of equilibrium and the magnetization produced can be detected in magnetic resonance signals with receive coils not shown in the figure. The general functions for creation of magnetic resonance signals with various imaging sequences are known to the person skilled in the art, so that no detailed explanation will be provided here.

The magnetic resonance device also has a central control computer 13, which is used for controlling the MR device. The central control unit 13 has a gradient controller 14 for controlling and switching the magnetic field gradients. An RF controller 15 is provided for controlling and applying the RF pulses for deflecting the magnetization. In a memory unit 16 for example the imaging sequences necessary for the recording of the MR images can be stored, as well as other programs which are necessary for operating the MR apparatus. A recording unit 17 controls the image recording and thus controls, as a function of the chosen imaging sequence, the order in which magnetic field gradients and RF pulses will be applied. Thus the recording unit 17 also controls the gradient controller 14 and the RF controller 15. The MR images computed in a processing unit 20 can be displayed on a display 18 and an operator can operate the MR apparatus via an input unit 19.

Figure 2:
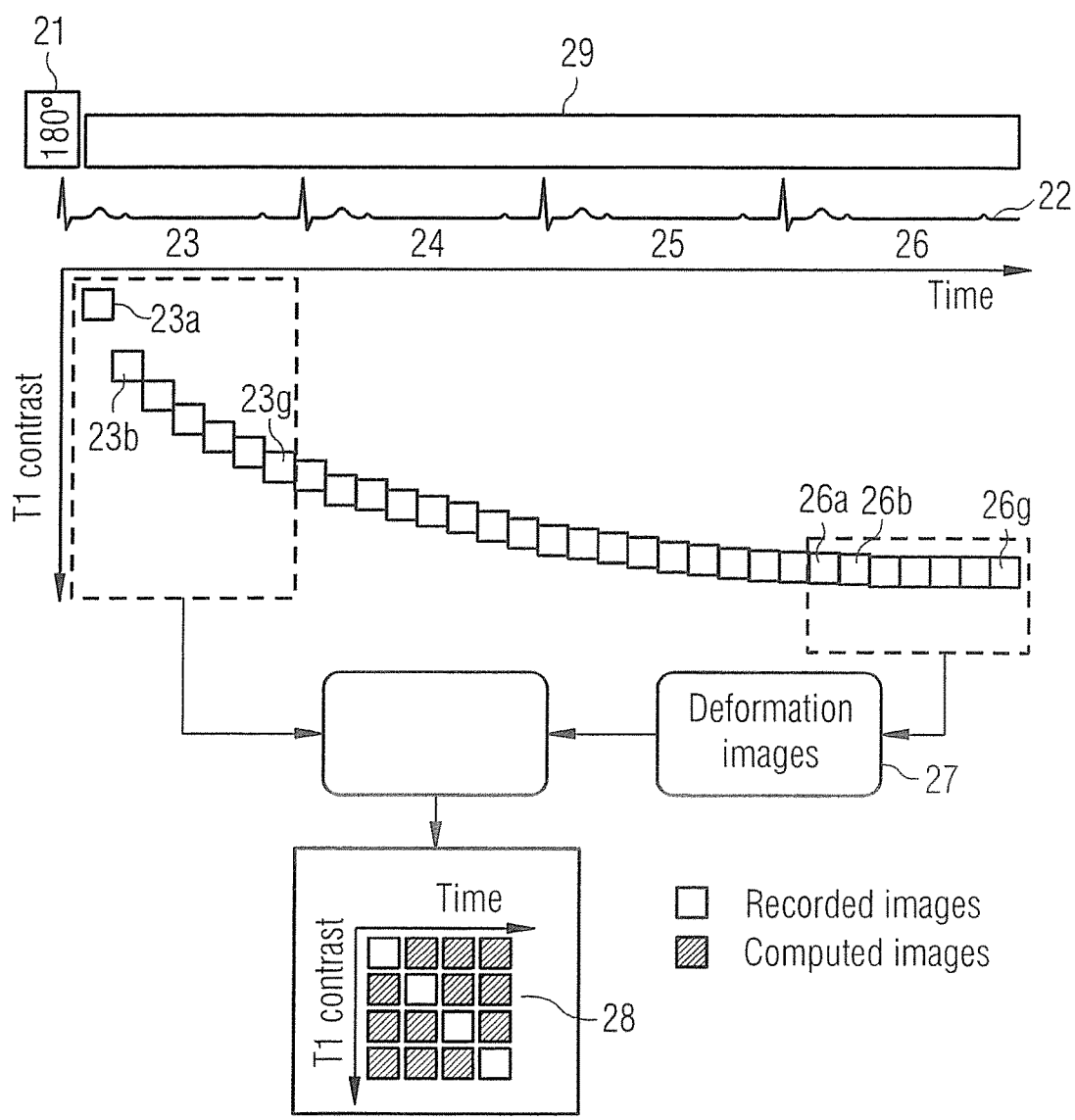
FIG. 2 is a schematic diagram illustrating how the movement-corrected MR images are computed.

FIG. 2 is a schematic diagram of a part of the imaging sequence and the post-processing steps with which recordings of the heart, for example so-called delayed-enhancement examinations, can be carried out after administration of contrast medium. After application of an RF pulse 21, here an inversion pulse, which occurs as an EKG-triggered pulse through EKG triggering 22, the images are recorded during a period of time that is represented schematically by the bar 29. The image recording can for example involve a bSSFP sequence, which uses a compressed-sensing technology with a k-t regularization. For example 2D MR data is recorded after the inversion pulse 21, which is applied immediately after the R edge of the EKG. In the case shown the images are recorded over four heart cycles: a heart cycle 23, a heart cycle 24, a heart cycle 25 and a heart cycle 26. The temporal resolution of the MR images recorded during the various heart cycles can lie between 30 and 40 ms, so that a number of images are recorded per heart cycle.

FIG. 2 also schematically shows the contrast which the individual MR images have in the individual heart cycles. As can be seen, the contrast between the individual MR images 23a-23g of the first heart cycle 23 varies very greatly because of the inversion pulse just applied. The magnetization approaches its state of equilibrium over the recording time so that, in cycle 26, the difference in the magnetization between the individual MR images is now only small.

The recording takes place over at least two cycles, wherein in a first cycle, cycle 23, the magnetization change from MR image to MR image is greater than in a second cycle, in the case shown the cycle 26. The MR images 26a-26g of the cycle 26 are now used to compute movement information of the moving heart, for example deformation information. Since the individual MR images 26a-26g exhibit a small difference in contrast, the heart movement can be well determined with these images, since no tissue-related contrast differences between the individual images occur. How a registration of the individual MR images for various heart phases to one another is possible and how individual deformation images showing the deformation of the heart in the various heart phases can be computed from this is known to the person skilled in the art and is not explained in any greater detail here. A possible computation of the movement information is described in "Efficient Symmetric and Inverse-Consistent Deformable Registration Through Interleaved Optimization", Christoph Guetter, Hui Xue, Christophe Chefd'hotel, Jens Guehring, Biomedical Imaging: From Nano to Macro, 2011 IEEE International Symposium, pages: 590-593, ISSN: 1945-7928. These deformation images which are obtained from the MR images of the second cycle, here of the last cycle 26, are shown schematically in FIG. 2 in field 27. Thus the heart movement is identified and can be applied to the MR images 23a-23g, which were recorded in the first heart cycle. As will be explained in conjunction with FIGS. 3 and 4, it is thus possible to determine from the deformation information, for the individual contrasts of the first cycle in each case, MR images for the different phases of the cyclic movement, as is shown schematically by the matrix 28.

The deformation information described above can be based on the inherent movement of the heart. If a residual movement is still present because the breath has not been held completely, i.e. a movement through the movement of the surroundings, this can likewise still be corrected. If between the two cycles 23 and 26 a slight movement is still present, for example through slight breath activity, this can be compensated for before the determination of the movement information by registration of the MR images of the various cycles with one another. Here, for example, the last image from the first cycle, image 23g, can be registered with the last image of the second cycle, image 26g. The second movement information produced here can then be applied to all the MR images of the second cycle. In general MR images of the same movement phase from the two cycles can be compared with one another in order to compute second movement information from this.

Figure 3:
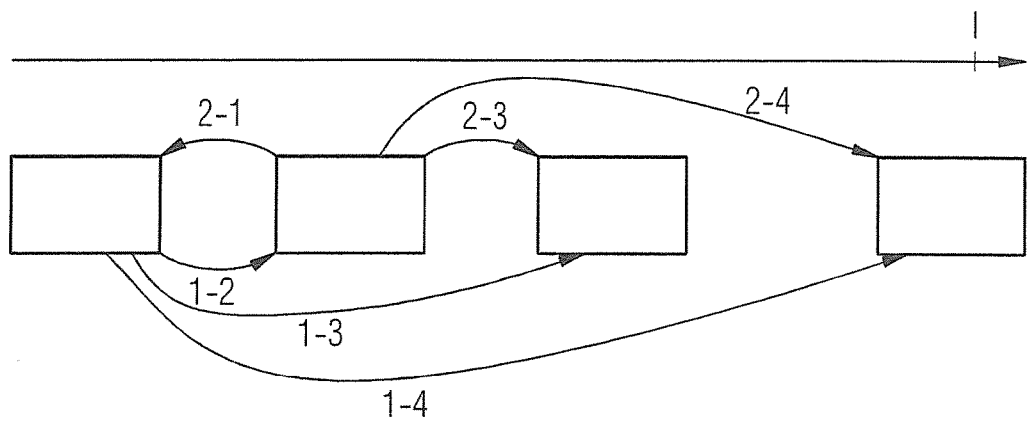
FIG. 3 shows a procedure for explaining the computation of the movement information for the various movement phases.

With reference to FIG. 3 it is first explained which movement or deformation information is determined. To this end, FIG. 3 shows schematically the various movement phases of a heart cycle, wherein, in the case shown, four movement phases are shown. Naturally it is possible to divide the cyclic movement into more or fewer different movement phases. The individual MR images 26a-26g are assigned to the movement phases or each image represents one movement phase, wherein for each movement phase at least one MR image is present. In the example shown in FIG. 2, eight images have been recorded per cycle. This number can vary and has only been used for illustration purposes. If the MR image or MR images of the first movement phase are compared with the MR images of the second movement phase, then the change in movement is able to be determined, which has been produced from the first phase relative to the second movement phase. This is indicated schematically in FIG. 3 by the arrow 1-2. Likewise the movement or deformation change from the first phase relative to the third phase can be determined, shown in the image by 1-3, and the movement change from the first to the fourth phase is shown by 1-4. Furthermore, the movement change from the second phase relative to the first phase or from the second relative to the third or fourth phase can be computed, so that the movement change from each of the movement phases to each of the other movement phases is computed. If the movement is divided into n different movement phases within the cycle, then n(n−1) items of movement or deformation information are produced. This movement or deformation information can contain translation or rotation components. With the movement information determined in this way it is now possible for the MR images of the first cycle to determine MR images for the various movement phases.

Figure 4:
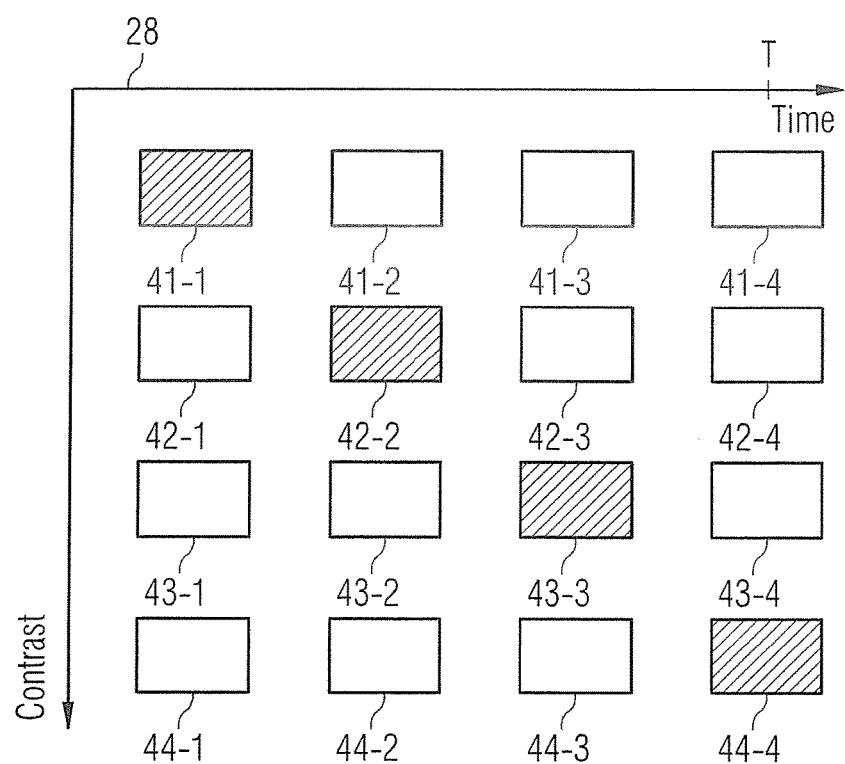
FIG. 4 shows a matrix presenting the computed and recorded MR images as a function of the movement phase and the contrast.

This is explained in greater detail in FIG. 4, where the matrix 28 from FIG. 2 is shown once again in detail. The MR images depicted cross-hatched in FIG. 4 are MR images which were recorded in the respective cycle by the MR apparatus, in the case shown 41-1, 42-2, 43-3 and 44-4. These four MR images can for example be any of the MR images 23a-23g from FIG. 2. The recorded MR image 41-1 has a first contrast, for example since it was recorded directly after the application of the inversion pulse. With the use of the deformation images, which were computed, as explained in FIG. 3, the MR images 41-2, 41-3 and 41-4 can now be computed. Referring to the example of FIG. 3, the deformation information 1-2, 1-3 and 1-4 has been used here, starting from the recorded MR image 41-1, to compute the images 41-2 to 41-4. Thus a sequence of MR images is provided for a first contrast, which for example can be used for a CINE representation of the moving heart in the first contrast. A similar computation is possible for the MR images 42. Starting from the recorded MR image and the movement information, here the movement information 2-1, 2-3 and 2-4, the MR images 42-1, 42-3 and 42-4 are computed, so that a sequence of MR images has been computed for a further other contrast. In the same way, the MR images 43-1 to 43-4 and 44-1 to 44-3 can be computed. As can be seen schematically in FIG. 4, for different contrast values per sequence of MR images four different movement phases are produced in each case by this. These sequences of MR images can be assessed by a doctor in order to obtain, for the various contrast values, information for the movement of the myocardium.

It is further possible, from the development of the magnetization, as is shown in FIG. 2, to compute T1 and T2 values, for example by a 3-parameter fit, based on voxels of the created images.

Figure 5:
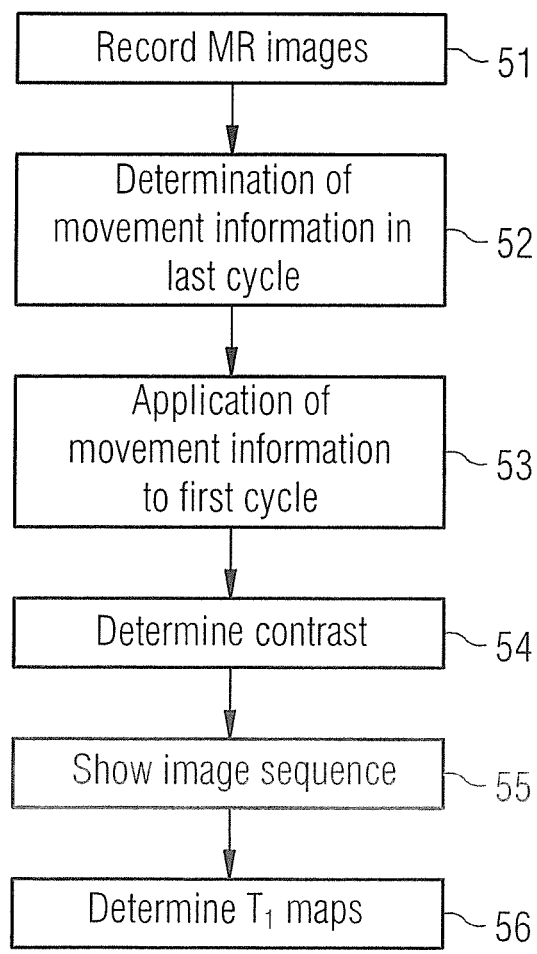
FIG. 5 is a flowchart with steps carried out during the computation of the MR images with variable contrast in accordance with the invention.

In FIG. 5 the individual steps are summarized schematically. The recording of the MR images takes place in step 51, wherein, as has been shown in FIG. 2, before the recording of the MR images, an inversion pulse or a preparation pulse can be applied. As mentioned initially, however, an inversion pulse or preparation pulse is not absolutely necessary to create a magnetization process which approaches the state of equilibrium. Subsequently, in step 52, movement information can be determined from the MR images of the second of the at least two cycles, wherein, in the example of FIG. 4, this was the fourth cycle or the last during the recording of the MR images. In step 53 this movement information is applied to the MR images of the first cycle, in order, as shown in FIG. 4, to compute the MR images for the various contrast values for the various movement phases of the cyclic movement. Subsequently, after the image recording, a contrast in which the user requires the presentation can be determined by a user in step 54. This means that any given contrast can be chosen only afterwards, rather than before the recording of the MR images in step 51. In step 55 the image sequence can then be presented with the desired chosen contrast, for example for a CINE presentation. As an option it is possible, in step 56, to compute T1 and T2 values for the individual pixels from the magnetization curve, as shown in FIG. 2, by fitting to a curve.

In the embodiment described above, the movement information of the last cycle, of the so-called second cycle, has only been applied to the MR images of the first cycle. It is also possible, referring to FIG. 2, to apply the movement information of the last cycle to the MR images of the second cycle (the cycle 24), which have contrast values other than those in the first cycle 23. Although the contrast differences in cycle 24 are no longer as large as in cycle 23, the use of the movement information is not restricted to the MR images of the first cycle 23; an application to the first cycles 23, 24 is likewise conceivable.

In summary the invention described herein makes possible the creation of MR images with a sufficient spatial and temporal resolution at various contrasts.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating magnetic resonance (MR) images of an examination object that performs a cyclic cardiac movement, with each cycle in said cyclic cardiac movement being divisible into successive movement phases, said movement phases being comparable from cycle-to-cycle, said method comprising:

from a control computer, operating an MR scanner, while the examination object is situated therein, to acquire MR signals from the examination object over at least two cycles of said cyclic movement by acquiring, in each of said at least two cycles, a plurality of MR data sets respectively for a plurality of MR images wherein, over said at least two cycles, a magnetization given to nuclear spins of the examination object, that influences said MR data sets, is changing toward a state of equilibrium of said nuclear spins and wherein, in a second data set of said at least two cycles, said magnetization is closer to said state of equilibrium than in a first of said at least two cycles;

in said control computer, determining movement information representing the respective movement phases in the second of said cycles, using the MR data sets acquired during said second of said cycles, with said movement information of the examination object being determined individually for each of said respective movement phases in the second of said cycles;

in said control computer, executing a movement correction for correcting for said cyclic movement of said examination object in said first of said cycles by applying said movement information individually for the respective movement phases of the cyclic movement in said first of said cycles using the movement information determined individually for the respective movement phases in the second of said cycles;

in said control computer, reconstructing MR images of the respective movement phases of said first of said cycles by executing a movement-corrected reconstruction wherein movement of the examination object in each of said movement phases of said first cycle is corrected using said movement information determined for said movement phases of said first of said cycles; and providing the reconstructed MR images available at an output of said control computer in electronic form, as an image data file.

2. A method as claimed in claim 1 comprising, in said control computer, for each of said respective movement phases of the examination object in said second of said cycles, determining a movement change relative to each of the other respective movement phases in said second of said cycles, and executing said movement correction algorithm for said MR data sets of said first of said cycles to produce a movement corrected MR image for each of the respective movement phases in said first of said cycles.

3. A method as claimed in claim 1 comprising:
   at a display in communication with said control computer, displaying each of said MR images with a contrast value; and
   reconstructing said MR images to produce a contrast change between temporally adjacent MR images of said first of said cycles that is greater than for temporally adjacent MR images of said second of said cycles.

4. A method as claimed in claim 1 comprising, in said control computer:
   executing said reconstruction to give each MR image of said first of said cycles a different contrast value, and to assign a respective movement phase of said first of said cycles to each reconstructed MR image of said first of said cycles;
   for the respective contrast values, reconstructing at least one initial MR image acquired with the respective contrast value and using the movement information for said initial reconstructed MR image to reconstruct movement-corrected MR images for the other movement phases of said first of said cycles, with the same contrast value as the associated initial MR image.

5. A method as claimed in claim 4 comprising after reconstructing said movement-corrected MR images, MR images for all contrast values of said first of said cycles and for all movement phases of said cyclic movement are present as reconstructed MR images.

6. A method as claimed in claim 1 comprising using the acquired MR images and the reconstructed movement-corrected MR images for reconstructing spatially-resolved T1 and T2 relaxation times of said examination object.

7. A method as claimed in claim 6 wherein said examination object is the heart of a patient, and comprising acquiring said MR data sets over a plurality of cardiac cycles between three and six.

8. A method as claimed in claim 1 comprising, from said control computer, operating said MR scanner to prepare said magnetization by applying a preparation pulse, that starts said changing of said magnetization toward said equilibrium state, before acquiring said MR data sets.

9. A method as claimed in claim 8 comprising applying said preparation pulse as an inversion pulse that inverts said magnetization.

10. A method as claimed in claim 8 wherein said first of said cycles is the first-occurring cycle in time after said preparation pulse, and wherein said second of said cycles follows said first of said cycles.

11. A method as claimed in claim 1 comprising, from said control computer, operating said MR scanner to cause said magnetization to approach said state of equilibrium by radiating a plurality of radio-frequency (RF) pulses at an interval that is smaller than the T1 time of the examination object.

12. A method as claimed in claim 1 wherein said first of said cycles is a first-occurring cycle in said cyclic movement during which said MR data sets are acquired, and wherein said second of said cycles is a last cycle in said cyclic movement in which said MR data sets are acquired.

13. A method as claimed in claim 1 comprising generating said movement information to comprise first movement information dependent on movement of an organ as said examination object, and second movement information accounting for movement of said organ by movement of an environment of said organ, and determining said second movement information by registering a reconstructed MR image of said first of said cycles with a reconstructed MR image of a second of said cycles, both in a same movement phase.

14. A magnetic resonance (MR) apparatus comprising:
   an MR scanner adapted to receive an examination object that performs a cyclic cardiac movement, with each cycle in said cyclic respiratory movement, with each cycle in cyclic cardiac movement being divisible into successive movement phases, said movement phases being comparable from cycle-to-cycle;
   a control computer configured to operate said MR scanner, while the examination object is situated in the MR scanner, to acquire MR signals from the examination object over at least two cycles of said cyclic movement by acquiring, in each of said at least two cycles, a plurality of MR data sets respectively for a plurality of MR images wherein, over said at least two cycles, a magnetization given to nuclear spins of the examination object, that influences said MR data sets, is changing toward a state of equilibrium of said nuclear spins and wherein, in a second data set of said at least two cycles, said magnetization is closer to said state of equilibrium than in a first of said at least two cycles;
   said control computer being configured to determine movement representing the respective movement phases in the second of said cycles, using the MR data sets acquired during said second of said cycles, with said movement information of the examination object being determined individually for each of said respective movement phases in the second of said cycles;
   said control computer being configured to execute a movement correction for correcting for said cyclic movement of said examination object in said first of said cycles by applying said movement information individually for the respective movement phases of the cyclic movement in said first of said cycles using the movement information determined individually for the respective movement phases in the second of said cycles;
   said control computer being configured to reconstruct MR images of the respective movement phases of said first of said cycles by executing a movement-corrected reconstruction wherein movement of the examination object in each of said movement phases of said first cycle is corrected using said movement information determined for said movement phases of said first of said cycles; and
   said control computer being configured to provide the reconstructed MR images at an output of said control computer in electronic form, as an image data file.

* * * * *